US006713262B2

United States Patent
Gellibolian et al.

(10) Patent No.: US 6,713,262 B2
(45) Date of Patent: Mar. 30, 2004

(54) METHODS AND COMPOSITIONS FOR HIGH THROUGHPUT IDENTIFICATION OF PROTEIN/NUCLEIC ACID BINDING PAIRS

(75) Inventors: Robert Gellibolian, Fremont, CA (US); Eric M. Leproust, Campbell, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/180,437

(22) Filed: Jun. 25, 2002

(65) Prior Publication Data

US 2003/0235828 A1 Dec. 25, 2003

(51) Int. Cl.[7] .................. C07H 21/04; C07H 19/04; C12Q 1/68; C12Q 1/70; C12P 19/34; A61K 38/00; C07K 1/00
(52) U.S. Cl. .................. 435/6; 435/5.6; 435/91.2; 530/300; 530/333; 530/350; 536/24.3; 536/24.33; 536/26.6
(58) Field of Search ................ 435/6, 5, 91.2; 536/24.3, 24.33, 26.6; 530/300, 333, 350

(56) References Cited

U.S. PATENT DOCUMENTS

| | | | | |
|---|---|---|---|---|
| 5,556,752 A | * | 9/1996 | Lockhart et al. ............... | 435/6 |
| 5,753,439 A | * | 5/1998 | Smith et al. .................... | 435/6 |
| 5,925,517 A | | 7/1999 | Tyagi et al. | |
| 6,150,097 A | | 11/2000 | Tyagi et al. | |
| 6,355,421 B1 | * | 3/2002 | Coull et al. ..................... | 435/6 |

* cited by examiner

Primary Examiner—Kenneth R. Horlick
Assistant Examiner—Young Kim

(57) ABSTRACT

Methods and compositions for high-throughput identification of protein/nucleic acid binding pairs are provided. In the subject methods, a nucleic acid probe array, e.g., a molecular beacon probe array, is contacted with a target nucleic acid population to produce a hybridized array. The resultant hybridized array is then contacted with a population of proteins to produce a protein bound array. Any resultant array surface bound target nucleic acid/protein complexes are then detected to identify protein/nucleic acid binding pairs. In certain embodiments, the protein and/or nucleic acid members of the identified protein/nucleic acid binding pairs are further characterized. Also provided are systems and kits for use in practicing the subject methods. The subject invention finds use in a variety of different applications.

31 Claims, 4 Drawing Sheets

METHODS AND COMPOSITIONS FOR HIGH THROUGHPUT IDENTIFICATION OF PROTEIN/NUCLEIC ACID BINDING PAIRS

FIELD OF THE INVENTION

The field of this invention is molecular biology, particularly protein/nucleic acid binding interactions and protocols for the identification thereof.

BACKGROUND OF THE INVENTION

Identification of protein-nucleic acid interactions is paramount in understanding the underlying molecular mechanisms in cellular processes such as replication, transcription, and signaling. One important component in the characterization of DNA/RNA binding proteins is the analysis of sequence specific interactions using "footprinting" techniques, in which the sequence of the protein binding domain of a nucleic acid is identified.

One footprinting protocol that finds use is based on ligation mediated polymerase chain reaction (LMPCR) (Mueller, P. R. and Wold, B. (1989) *Science* 246: 780–786). Reagents that are commonly employed in this protocol include DNaseI, DMS (dimethylsulfate) and UV light. In these footprinting protocols, a given nucleic acid, typically of known sequence, is screened for the presence of protein binding sequences by contacting the nucleic acid with one or more test nucleic acid binding proteins. Specific sequences along the nucleic acid that are bound to the protein(s) are protected from nucleophilic attack or cross-linking by the reagents, thus creating a "footprint" across this region(s) in the nucleic acid. The protected region is then identified by first cleaving the DNA at the lesion, and annealing a gene specific primer to the region of interest. This primer is extended using a processive DNA Polymerase to the cleavage site, creating a blunt end. A unidirectional linker (staggered) is then attached to the blunt ended molecule using DNA ligase. The 3' end of the longer strand of the linker is ligated to the 5' end of the genomic DNA. The shorter strand of the linker lacks a 5' phosphate and therefore is not ligated to the extension product. A second gene specific primer and a linker specific primer are annealed to this product, which is now a suitable substrate for a PCR reaction. Only molecules that have both sequences (primer 2 sequence and linker sequence) are amplified. A third gene specific primer (labeled) is then used to sequence the products that can subsequently be visualized on a sequencing gel. In this manner, the protein binding sequence of the nucleic acid is identified.

Terminal Transferase dependent PCR (TDPCR) is a modified LMPCR methodology that has been devised for studying protein-RNA interactions (Tornaletti, S, and Pfeifer, G (1995) *J. Mol. Biol.* 249: 714–728; Chen, H—H, et al. (2000) *Nucl. Acid Res.* 28: 1656–1664). It uses UV light as the primary source of creating appropriate lesions (intrastrand pyrimidine dimer formation, primarily between thymidines) within the RNA, which inhibit progression of DNA polymerases.

Although LMPCR and TDPCR are very powerful techniques in mapping protein-nucleic acid interaction or binding sites, they suffer from several disadvantages that are summarized below. First, in studying protein-nucleic acid interactions using LMPCR/TDPCR, one needs to have prior knowledge of the gene sequence (or transcript) in question in order to be able to design appropriate gene specific primers for amplification. Second, the LMPCR/TDPCR protocols are labor intensive and offer considerable challenges to those not well versed in the art. Third, both LMPCR and TDPCR allow analysis of protein-nucleic acid interactions at the nucleotide resolution by revealing the footprint that the protein leaves behind on the nucleic acid. However, they are not useful techniques in determining the underlying identity of the protein(s) resulting in such a footprint. To identify the proteins per se, one has to resort to the use of monoclonal antibody protocols, which suffer from the drawback that a priori knowledge about the identity of the proteins is needed. Because of the above limitations, none of the currently employed techniques for identifying protein/nucleic acid binding pairs can be adopted for high throughput mapping of site-specific protein binding sequences.

As such, there is a continued interest in the development of new protocols for identifying protein/nucleic acid binding pairs, where the development of a protocol that could be adapted to a high throughput format is of particular interest.

Relevant Literature

U.S. Patents of interest include: U.S. Pat. Nos. 5,925,517; 6,150,097; 6,355,421. Also of interest is: Tyagi & Kramer, Nat Biotechnol (1996 Mar) 14(3): 303–8.

SUMMARY OF THE INVENTION

Methods and compositions for identifying protein/nucleic acid binding pairs are provided. In the subject methods, a nucleic acid probe array is first contacted with a target nucleic acid population to produce a hybridized array. The resultant hybridized array is then contacted with a population of proteins to produce a protein bound array. Protein/nucleic acid binding pairs are then detected on the array surface. In certain embodiments, the protein and/or nucleic acid members of the identified protein/nucleic acid binding pairs are further characterized.

In many embodiments, the array employed is a molecular beacon array having a plurality of distinct molecular beacon probes all labeled with the same first fluorescent label. In these embodiments, the molecular beacon array is first contacted with a target nucleic acid population to produce a hybridized array. The resultant hybridized array is then contacted with a population of proteins all labeled with the same second fluorescent label to produce a protein bound array. A feature of the methods of this embodiment is that the first and second fluorescent labels make up a FRET pair. Any FRET generated signals from the resultant protein bound array are then detected from the protein bound array to identify protein/nucleic acid binding pairs.

Also provided are systems and kits for use in practicing the subject methods. The subject invention finds use in a variety of different applications.

DESCRIPTION OF THE SPECIFIC EMBODIMENTS

Figure 1:
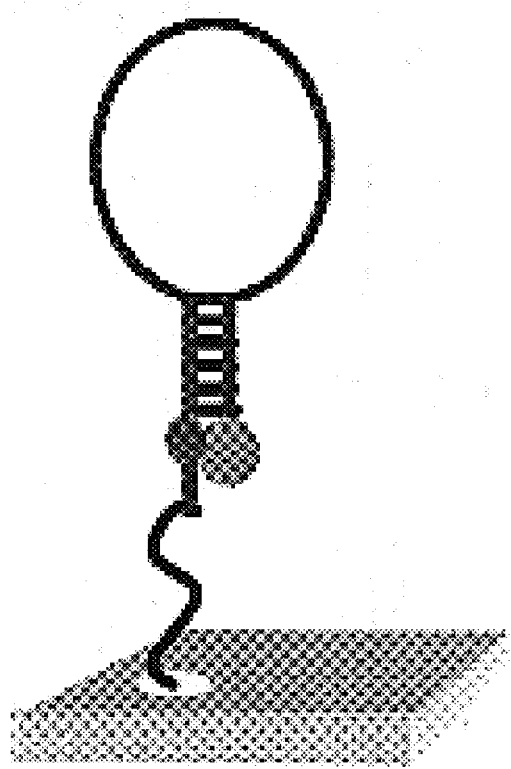
FIG. 1 provides a view of a representative molecular beacon probe of the molecular beacon arrays employed in certain embodiments of the subject invention.

Methods and compositions for high-throughput identification of protein/nucleic acid binding pairs are provided. In the subject methods, a nucleic acid probe array, e.g., a molecular beacon probe array, is contacted with a target nucleic acid population to produce a hybridized array. The resultant hybridized array is then contacted with a population of proteins to produce a protein bound array. Any resultant array surface bound target nucleic acid/protein complexes are then detected to identify protein/nucleic acid binding pairs. In certain embodiments, the protein and/or nucleic acid members of the identified protein/nucleic acid binding pairs are further characterized. Also provided are systems and kits for use in practicing the subject methods. The subject invention finds use in a variety of different applications.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing various invention components that are described in the publications, which might be used in connection with the presently described invention.

As summarized above, the subject invention provides methods and compositions for the high-throughput identification of protein/nucleic acid binding pairs. In further describing the subject invention, the methods will be described first in greater detail, followed by a review of the systems and kits provided by the invention for practicing the subject methods.

As summarized above, the subject invention provides methods for the high-throughput identification of protein/ nucleic acid binding pairs. More specifically, the subject invention provides methods of identifying protein/nucleic acid binding pairs that exist in a union of a first set of one or more nucleic acids and a second set of one or more proteins. The nucleic acid member of the identified binding pairs may be RNA, e.g., cRNA, mRNA etc., or DNA, e.g., single stranded or double stranded DNA. As such, RNA/ protein binding pairs and DNA/protein binding pairs may be identified by using the subject invention. The sets of nucleic acids and proteins that are screened or assayed according to the subject methods may be obtained from a variety of sources, including naturally occurring or synthetic sources. In addition, the sources of the proteins and nucleic acids that make up the assayed sets may be the same or different.

In practicing the subject methods, a nucleic acid probe array is employed to assay the union of a set of nucleic acids and proteins for the presence of protein/nucleic acid binding pairs in the union. To assay the union of the nucleic acid and protein sets, the nucleic acid probe array is first contacted with a population of target nucleic acids, i.e., the set of target nucleic acids, to produce a hybridized array. The resultant hybridized array is then contacted with a population of labeled proteins, i.e., the set of proteins, to produce a protein bound array. The resultant protein bound array is then assayed to detect any resultant surface bound labeled protein molecules in order to detect protein/nucleic acid binding pairs that exist in the union of the assayed nucleic acid and protein sets. Depending on the particular embodiment, the labeling protocol employed to detect the surface bound protein/nucleic acid complex may vary. Representative labeling protocols include those that employ directly detectable labels and those that employ indirectly detectable labels, where the latter of which are characterized by having two or more signal producing system members that work in concert to produce a detectable signal. Examples of directly detectable labels include isotopic labels, fluorescent labels, FET labeling systems, including FRET labeling systems, etc. Examples of indirectly detectable labels include those found in enzymatic signal producing systems, e.g., chemilumninescent systems, etc.

Because of the ease of use and detection of fluorescent labels, in many embodiments employed the labels employed are directly detectable fluorescent labels. Fluorescent labeling systems of interest include FET labeling systems, where energy transfer between donor and acceptor moieties occurs, where the acceptor may be a second fluorescer, e.g., as is present in FRET systems, or may be a quencher moiety. In certain embodiments of particular interest, a FRET labeling system is employed, where at least two of three main assay components (i.e., the array bound probe nucleic acids, the target nucleic acids, and the proteins) have labels that form a FRET pair, and in certain embodiments all three of these components have labels that form a FRET pair.

In many embodiments of particular interest, the array of probe nucleic acids that is employed is one that is a molecular beacon array. Since these embodiments are of particular interest, the invention will now be further described in terms of these embodiments.

In practicing the subject methods of these embodiments of particular interest, a molecular beacon array is employed to assay the union of a set of nucleic acids and proteins for the presence of protein/nucleic acid binding pairs in the union. To assay the union of the nucleic acid and protein sets, the molecular beacon array is first contacted with a population of target nucleic acids, i.e., the set of target nucleic acids, to produce a hybridized array. The resultant hybridized array is then contacted with a population of fluorescently labeled proteins, i.e., the set of proteins, to produce a protein bound array. The resultant protein bound array is then assayed for any resultant FRET generated signals, which signals are then detected in order to detect protein/nucleic acid binding pairs that exist in the union of the assayed nucleic acid and protein sets.

Molecular Beacon Array

As such, the first step in the subject methods is to provide a molecular beacon array for use in the subject methods. The molecular beacon array is a composition of matter that includes a substrate that displays at least one molecular beacon probe immobilized on a surface thereof, where the arrays employed in the subject invention typically include a plurality of distinct molecular beacon probes immobilized on a surface of a substrate, where each member of the plurality differs in terms of probe sequence, as described in greater detail below.

The molecular beacon probes of the subject arrays are conformationally labeled probe structures that generate a different fluorescent signal depending on whether or not they are hybridized to a target nucleic acid. In other words, the molecular beacon probes are probes that generate a first fluorescent signal, e.g., a quenched signal, undetectable signal, when not hybridized to a target nucleic acid and a second fluorescent signal, e.g., an unquenched fluorescent signal, when hybridized to a target nucleic acid. While in principle any conformational probe that functions as described above may be employed, in many embodiments the probes have a molecular beacon structure.

Figure 2:
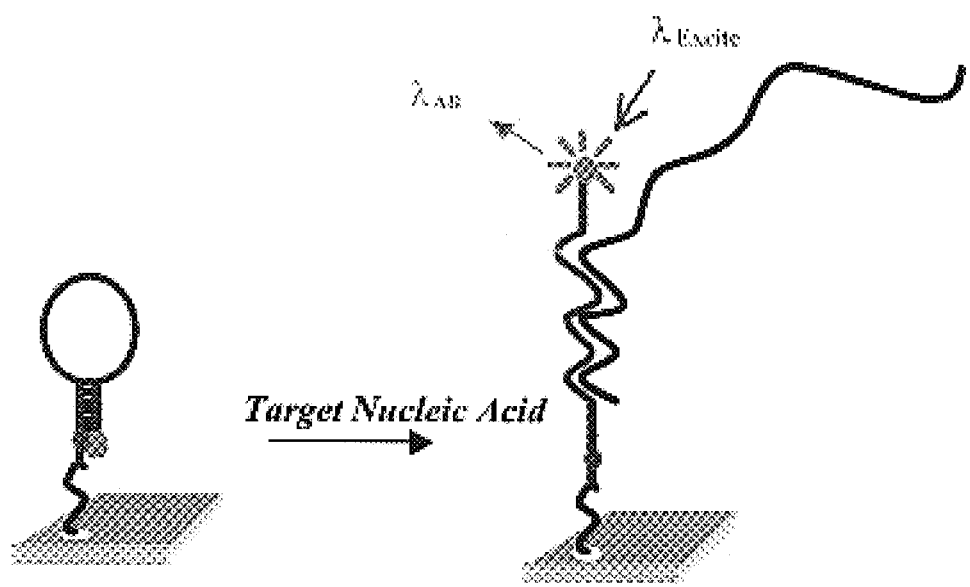
FIG. 2 provides an illustration of the hybridization of a target nucleic acid to a molecular beacon probe and the consequent conformational change of the molecular beacon probe to provide for a detectable signal.

Molecular beacon conformational probe structures are known to those of skill in the art and reviewed in, among other places, U.S. Pat. Nos. 5,925,517; 6,150,097 and 6,355,421 (the disclosures of which are herein incorporated by reference); as well as Tyagi & Kramer, Nat Biotechnol (1996 Mar) 14(3):303–8. Molecular beacons are single stranded nucleic acid or nucleic acid mimetic (e.g., PNA) probes that form a stem-loop structure. A fluorophore, i.e., first fluorescent label, and quencher are linked to opposite ends of the molecule. Fluorescence is quenched when the probe is in the stem-loop conformation. However, when the probe sequence in the loop anneals to a complementary nucleic acid target sequence, the duplex formed overcomes the shorter hairpin-stem so that the probe undergoes a conformational transition that separates the fluorophore and quencher, such that the signal generated by the first fluorescent label upon excitation is no longer quenched. FIGS. 1 and 2 provide a depiction of a representative molecular beacon probe in the two different conformations.

In the molecular beacon probes employed on the subject molecular beacon probe arrays, the probe sequence of the stem-loop structure is designed to hybridize to at least a portion of a target nucleic acid sequence. The probe sequence length may be any convenient length. In many embodiments, the length typically ranges from about 5 about 200 residues, e.g., nt, PNA subunits, etc. Often, the probing nucleobase sequence will be 5 to 150 nt in length, e.g., 10 to 100 nt in length, such as 50, 60, 70 nt in length, etc.

Flanking either side of the probe sequences in the molecular beacon probes are arm segments. The arm segments are designed to anneal to each other and thereby stabilize the interactions that fix the energy transfer of linked donor and acceptor moieties, i.e., first fluorescent label and quencher therefore, until the molecular beacon probe hybridizes to the target sequence. The arm segments may be of different lengths, but are typically the same length. The preferred length of the arm segments will depend on the stability desired for the interactions. However, the arm segments must not be so long that they prohibit hybridization to the target sequence. Often, the arm segments are from about 2 to about 10 subunits in length and more often from about 2 to about 5 subunits in length. In certain embodiments, both arm segments are external to the probing sequence.

Each molecular beacon probe is labeled such that the probe yields a quenched or unquenched fluorescent signal, depending on the conformation of the molecular beacon probe. The labels attached to the probes comprise a set of energy transfer moieties comprising at least one energy donor and at least one energy acceptor moiety. Typically, the set includes a single donor moiety and a single acceptor moiety. Nevertheless, a set may contain more than one donor moiety and/or more than one acceptor moiety. The donor and acceptor moieties operate such that the acceptor moiety accepts energy transferred from the donor moiety, resulting in quenching of the signal from the acceptor moiety.

In many embodiments, the donor moiety is a fluorophore. Representative fluorophores are derivatives of fluorescein, derivatives of bodipy, 5-(2'-aminoethyl)-aminonaphthalene-1-sulfonic acid (EDANS), derivatives of rhodamine, cyanine dyes, e.g., Cy2, Cy3, Cy 3.5, Cy5, Cy5.5, texas red and its derivatives, etc. Though the previously listed fluorophores might also operate as acceptors, in certain embodiments the acceptor moiety is a quencher moiety, e.g., a non-fluorescent aromatic or heteroaromatic moiety, e.g., 4-((-4-(dimethylamino)phenyl)azo) benzoic acid (dabcyl), etc.

Transfer of energy from the donor, e.g., first fluorescent label, may occur through collision of the closely associated moieties of a set or through a nonradiative process such as fluorescence resonance energy transfer (FRET). For FRET to occur, transfer of energy between donor and acceptor moieties of a set requires that the moieties be close in space (e.g., less than about 100 Å, often less than about 80 Å) and that the emission spectrum of a donor(s) have substantial overlap with the absorption spectrum of the acceptor(s). Alternatively, collision mediated (radiationless) energy transfer may occur between very closely associated donor and acceptor moieties whether or not the emission spectrum of a donor moiety(ies) has a substantial overlap with the absorption spectrum of the acceptor moiety(ies). This process is referred to as intramolecular collision since it is believed that quenching is caused by the direct contact of the donor and acceptor moieties.

The molecular beacon probes are generally polymeric and may be nucleic acids, polymeric mimetics thereof, e.g., PNAs, or copolymers of nucleotide and non nucleotide residues, e.g., block copolymers of nucleic acids and nulceic acid mimetics, such as PNAs. The nature of the molecular beacon probes may vary, so long as that function as described above.

As indicated above, in many embodiments an array of the above-described molecular beacon probes is employed. The molecular beacon probe arrays include at least two distinct molecular beacon probes that differ from each other with respect to their probing sequence, and yet are labeled with the same first fluorescent label, e.g., donor label, as described above. The molecular beacon probes of the array are immobilized. on e.g., covalently (such as cross-linked or directly synthesized through phosphoramidite linkage chemistry) or non-covalently (such as through biotin/avidin binding pair) attached to, different and known locations on the substrate surface. The probes may be attached to the surface directly, or through a suitable spacer group, as is known in the array art. Each distinct molecular beacon probe of the array is typically present as a composition of multiple copies of the probe on the substrate surface, e.g., as a spot or feature on the surface of the substrate. The number of distinct probes, and hence spots or similar structures, present on the array may vary, but is generally at least 1000, and may be as high as 25,000 or higher. The spots of distinct probes present on the array surface are generally present as a pattern, where the pattern may be in the form of organized rows and columns of spots, e.g. a grid of spots, across the substrate surface, a series of curvilinear rows across the substrate surface, e.g. a series of concentric circles or semi-circles of spots, and the like. The density of spots present on the array surface may vary, but will generally be at least about 10 and usually at least about 100 spots/cm$^2$, where the density may be as high as $10^6$ or higher, and in certain embodiments will generally not exceed about $10^5$ spots/cm$^2$. A variety of different array configurations and formats, including choice of substrate material, organization of probes, dimensions, etc., are known and have been developed, where any convenient configuration may be employed. Representative configurations of interest include, but are not limited to, those described in U.S. Pat. Nos. 6,372,483; 6,355,421; 6,323,043; 6,306,599; 6,242,266; 6,222,030; 6,221,653; 6,180,351; 6,171,797; and 6,077,674; the disclosures of which are herein incorporated by reference.

In certain embodiments, two or more distinct probes on the array form a set of probes that all hybridize to the same target nucleic acid, where the probe sequences of the different members of the set each hybridize to different domains or regions of the same target nucleic acid. See e.g., FIG. 4, where two probes that hybridize to the same target nucleic acid at different locations are illustrated. In certain embodiments, the arrays include sets of molecular probes that span the entire length of a target nucleic acid, such that the entire sequence of the target nucleic acid is represented among the different molecular beacon probes of the set that all hybridize to that target nucleic acid—in other words, a "tiled" set of molecular beacon probes is provided for a target nucleic acid. Such embodiments find use in. applications where characterization of the cognate sequence of an identified protein/DNA binding pair is desired, as described more fully below.

Target Nucleic Acid Hybridization

The next step in the subject methods is to bind the solid support bound molecular beacon probe(s), e.g., molecular beacon array, with one or more target nucleic acids under hybridization conditions to produce a hybridized array. In the broadest sense, the target nucleic acid(s) contacted with the array in this step is any nucleic acid, which is to be screened or assayed together with a protein set to identify whether it is part of a protein/nucleic acid binding pair. As such, the length, chemical nature and source of the target nucleic acid(s) may vary greatly, depending on the particular protocol being performed. The nucleic acids may be oligonucleotides, polynucleotides etc. The nucleic acid may be RNA, e.g., cRNA, mRNA, etc., or DNA, including either single stranded or double stranded DNA, e.g., cDNA, etc.

In many embodiments, a plurality of distinct nucleic acids are contacted with the molecular beacon array, e.g., 5 different, 50 different, 100 different, 500 different, 1000 different, 10,000 different, etc., nucleic acids of differing sequence.

The plurality of target nucleic acids that is contacted with the molecular beacon array may be generated using any convenient target nucleic acid generation protocol, where representative target generation protocols include both linear and geometric amplification protocols, where the generated target nucleic acids may be DNA, RNA etc. In many protocols known to those of skill in the art, an initial nucleic acid biological source is employed, e.g., a cellular or tissue nuclear source. Any convenient nucleic acid source may be employed.

A representative protocol of particular interest in certain embodiments includes the linear amplification protocol described in U.S. Pat. No. 6,132,997, the disclosure of which is herein incorporated by reference.

In many embodiments, the protocol that is employed is one that generates unlabeled target nucleic acids, as a label element on the target nucleic acid is not employed and could, potentially though not necessarily, interfere with the signal producing system that is employed. If, however, the target nucleic acid is labeled, it is labeled with a moiety that does not adversely affect the signal producing system employed in the subject methods, as described in greater detail below.

Once generated, the population of target nucleic acids is contacted with the molecular beacon array under hybridization conditions to produce a hybridized array. In many embodiments, the hybridization conditions under which contact of the array and the target nucleic acids takes place are stringent hybridization conditions. The term "stringent hybridization conditions" as used herein refers to conditions that are compatible to produce duplexes on an array surface between complementary binding members, i.e., between probes and complementary targets in a sample, e.g., duplexes of nucleic acid probes, such as DNA probes, and their corresponding nucleic acid targets that are present in the sample, e.g., their corresponding cRNA analytes present in the sample. An example of stringent hybridization conditions is hybridization at 37° C. or higher and 0.1×SSC (15 mM sodium chloride/1.5 mM sodium citrate). Another example of stringent hybridization conditions is incubation at 42° C. in a solution: 50% formamide, 5×SSC (150 mM NaCI, 15 mM trisodium citrate), 50 mM sodium phosphate (pH7.6), 5×Denhardt's solution, 10% dextran sulfate, followed by washing in 0.5×SSC with 0.01% SDS followed by another wash of 0.06×SSC at about 65° C. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

Contact/binding of the target nucleic acid population with the molecular beacon array as described above results in the production of a hybridized array. As such, duplex nucleic acid structures are produced at any location where a target nucleic acid has hybridized to the probe sequence of a surface bound molecular beacon probe. At these locations of the array, the hybridization of the target nucleic acid to the probe results in a conformational change of the probe, as illustrated in FIG. 2.

Optionally, following production of the target hybridized nucleic acid array, the hybridized array may be scanned or read, e.g., using conventional fluorescence detection techniques as described in greater detail below, to identify the target nucleic acids present in the contacted target nucleic acid population.

Protein Binding

Following production of the hybridized molecular beacon array, and any signal detection step, e.g., fluorescence scanning step (as mentioned above and described in greater detail below), the hybridized array is contacted with at least one labeled protein. A feature of the labeled protein is that it includes a second fluorescent label which, together with the first fluorescent label of the surface bound molecular beacon, produces or makes up a FRET pair. Two fluorescent labels are viewed as being a FRET pair for purposes of the present invention if, when positioned sufficiently close to each other (typically less than about 100 Å, and usually less than about 80 Å), they participate in fluorescence resonance energy transfer, such that excitation of one of the labels gives rise to emission from the other of the two labels. A variety of FRET pairs of fluorescent labels are known to those of skill in the art and may be employed. The energy donors of the pairs will generally be compounds which absorb in the range of about 300 to about 800 nm, more usually in the range of about 450 to about 700 nm, and are capable of transferring energy to an acceptor fluorophore, which generally absorbs light of a wavelength 15 nm, more usually 20 nm or higher, than the absorption wavelength of the donor. The acceptor will generally emit in the range of about 400 to about 900 nm. Fluorophores of interest include, but are not limited to: fluorescein dyes (e.g., 5-carboxyfluorescein (5-FAM), 6-carboxyfluorescein (6-FAM), 2',4',1,4,-tetrachlorofluorescein (TET), 2',4', 5',7', 1,4-hexachlorofluorescein (HEX), and 2',7'-dimethoxy-4',5'-dichloro-6-carboxyfluorescein (JOE)), cyanine dyes such as Cy5 and Cy3, dansyl derivatives, rhodamine dyes (e.g., tetramethyl-6-carboxyrhodamine (TAMRA), and tetrapropano-6-carboxyrhodamine (ROX)), DABSYL, DABCYL, anthraquinone, nitrothiazole, and nitroimidazole compounds, and the like. Fluorophores of interest are further described in WO 01/42505 and WO 01/86001, as well as the priority U.S. Applications of these documents, the disclosures of the latter of which are herein incorporated by reference.

Any convenient protocol may be employed to produce the labeled protein, as described above. In certain embodiments, the protein of interest is labeled with functionalized label reagent that covalently bonds to the protein and, in doing so, labels the protein. In these embodiments, the protein is contacted with functionalized label under conditions sufficient for a functional moiety of the protein, e.g., an amine or hydroxyl group, to react with the corresponding functional moiety present on the label to produce a covalent bond between the label and the analyte. As such, functionalized labels employed in these embodiments of the subject methods include a functional moiety and a label moiety. The functional moiety of the functionalized labels may vary greatly, and is chosen in view of the functional moiety present on the protein to be labeled, e.g., amine groups on the protein. In other words, the functional moiety present on the functionalized label is one that reacts with the functional moiety present on the protein to produce a covalent bond between the protein and the label. Representative functional moieties that may be present on the label include: amino, sulfhydryl, sulfoxyl, aminosulfhydryl, azido, epoxide, isothiocyanate, isocyanate, anhydride, monochlorotriazine, dichlorotriazine, mono-or dihalogen substituted pyridine, mono- or disubstituted diazine, maleimide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the like.

In many embodiments, the hybridized array in this step in contacted with a population of different proteins, i.e., a protein set, where the proteins are all labeled with the same second fluorescent label. By population of different proteins is meant a plurality of proteins that differ from each other in terms of amino acid sequence, where the number of distinct or different proteins in the population is at least 2, usually at least 50, more usually at least 100, and often is much greater, e.g., at least about 500, at least about 1000, at least about 2000, at least about 5000 etc.

In many embodiments, the population of labeled proteins is produced by contacting an initial source of a plurality of different proteins with functionalized label, as described above. The initial source of different proteins may be any convenient source, e.g., a synthetic source, a naturally occurring source, e.g., a cell lysate, tissue homogenate, etc.

At least one fluorescently labeled-protein, i.e., the protein set, as described above, is contacted with the hybridized array under protein/nucleic acid binding conditions sufficient to produce a protein bound array. Contact may occur using any convenient protocol. As such, a fluid sample that includes the at least one fluorescently labeled protein may be applied to the substrate surface, flowed across the substrate surface, or the substrate surface may be immersed in the fluid sample, etc.

Binding/contact between the surface and sample including the at least one labeled protein is maintained for a period of time sufficient for binding between the protein and any recognized nucleic acid binding sequences present on the substrate surface to occur. As such, the substrate surface and the sample are incubated for a period of time and under conditions sufficient for binding between nucleic acids and proteins of a given protein/nucleic acid binding pair to occur. The sample and substrate are typically incubated for a period of time ranging from about 5 min to 2 hours, usually from about 15 min to 2 hours and more usually from about 30 min to 1 hour. The temperature during this incubation period generally ranges from about 0 to about 37° C. usually from about 15 to 30° C. and more usually from about 18 to 25° C. Where desired, the substrate and sample may be agitated during incubation, e.g., by shaking, stirring, etc.

Figure 3:
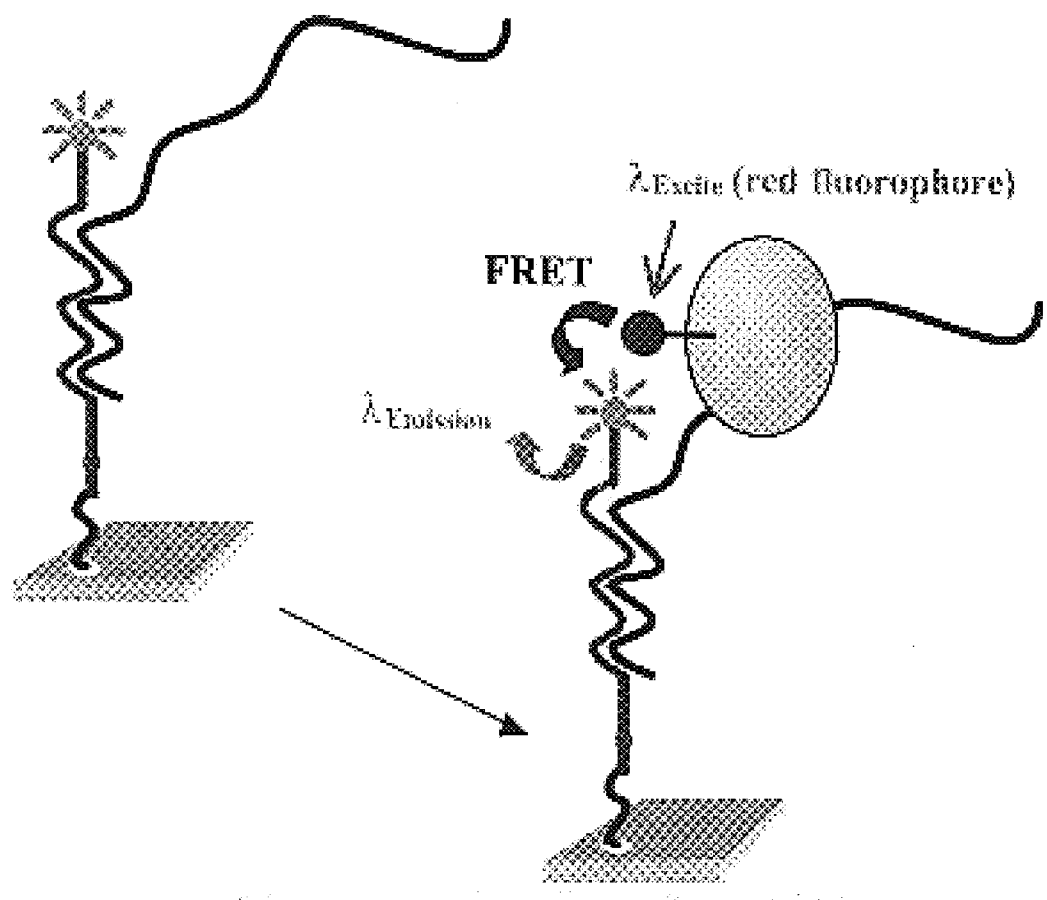
FIG. 3 provides an illustration of a protein bound to a target nucleic acid of a molecular beacon array, where the label of the protein and the label of the molecular beacon are in a FRET relationship.

The above contacting/incubating steps result in the production of a protein bound array, which includes one or more surface bound protein/nucleic acid binding pairs, if such pairs exist in the collection or union of target nucleic acid and labeled protein sets that are assayed according to the subject methods. The surface bound protein/nucleic acid binding pairs may have a structure as illustrated in FIG. 3.

FRET Signal Detection

Following production of the protein bound array, the surface of the array is assayed for the presence of FRET generated signal. Any convenient protocol for detecting FRET generated signal on the surface may be employed. Typically, this step involves irradiating the surface with a wavelength suitable for absorption of one of the fluorescent labels so that a FRET generated emission from the other of the fluorescent labels is produced, followed by detection of this FRET generated signal. Any convenient protocol for irradiating at the first wavelength and detecting the FRET emitted signal may be employed. As such, reading of the array may be accomplished by illuminating the array and reading the location and intensity of resulting fluorescence at each feature of the array to detect any protein/nucleic acid binding complexes on the surface of the array. For example, a scanner may be used for this purpose, which is similar to the AGILENT MICROARRAY SCANNER scanner available from Agilent Technologies, Palo Alto, Calif. Other suitable apparatus and methods are described in U.S. Pat. No. 6,583,424 "Reading Multi-Featured Arrays" by Dorsel et al.; and U.S. patent application Ser. No. 09/430,214 "Interrogating Multi-Featured Arrays" by Dorsel et al. These references are incorporated herein by reference.

Any detected FRET generated signals are then attributed to the presence of a protein/nucleic acid binding pair at the location of the surface from which the signal is generated. In this manner, detection of a FRET generated signal on the surface of the array is employed to detect a protein/nucleic acid binding pair on the surface of the array.

In certain embodiments, the hybridized array is contacted with two distinct populations of labeled proteins, which are differentially labeled. By differentially labeled is meant that the two populations are labeled with different fluorescent labels that are distinguishable from each other, e.g., upon excitation they emit at different maxima. Although the two populations are differentially labeled, the label of the first population and the label of the second population must nonetheless form a FRET pair with the first fluorescent label of the surface bound molecular beacon. In such embodiments, the two different protein populations are generally contacted/bound in known amounts relative to each other with the array, such that the ratio of amounts of first and second populations contacted/bound to the array is known. In certain embodiments, substantially equimolar, including equimolar, amounts of the first and second protein populations are contacted/bound with the array. Embodiments where two differentially labeled protein populations are bound with the hybridized array include applications where the identified protein/nucleic acid binding pairs are to be quantitated, where protein populations are to be compared, e.g., normal/control pairs; disease/normal pairs, etc.

Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing). In certain embodiments, the subject methods include a step of transmitting data from at least one of the detecting and deriving steps, as described above, to a remote location. By "remote location" is meant a location other than the location at which the array is present and hybridization and/or protein binding occurs. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

Identification of Protein/Nucleic Acid Binding Pairs

As indicated above, the data generated upon reading of the array is employed to identify protein/nucleic acid binding pairs that exist in the union of the set of proteins and nucleic acids that are assayed with the array according to the subject methods. More specifically, the data, i.e., FRET generated signal, is employed to identify protein/nucleic acid binding pairs that exist in the combined set of target nucleic acids and labeled proteins that are contacted with the molecular beacon array during practice of the subject methods. For example, where the target nucleic acid population and the labeled protein population contacted with the molecular beacon array are obtained from the same cellular/tissue source, any observed FRET generated signals indicate the presence of protein/nucleic acid binding pairs found in the cell/tissue source. In other embodiments where the target nucleic acid and protein populations are from different sources, FRET generated signals indicate protein/nucleic acid binding pairs present in the union of the two sets from different sources. As such, the array is scanned for the presence of FRET generated signals, where any observed signals indicate the presence of a protein/nucleic acid binding pair and therefore can be related to the presence of a protein/nucleic acid binding pair, i.e., the presence of a protein/nucleic acid binding pair can be derived from the observed FRET generated signal.

Optional Additional Steps

Following identification of the any protein/nucleic acid binding pairs, the identified protein/nucleic acid binding pairs may be further analyzed, e.g., to identify the nature of the protein member and/or nucleic acid member of the pair.

Protein Identification

The protein member of the protein/nucleic acid binding pair may be further characterized/identified using a number of different protocols, including protocols known to those of skill in the art. Basically, any convenient protocol may be employed, where the protocol yields additional information with regard to the nature/identity of the protein member of the identified protein/nucleic acid binding pair. One representative protein characterization protocol that may be employed is to produce an enzyme digest profile for the protein, where the protein is then compared to a reference database of digest profiles to identify the protein. For example, the protein member of the protein/nucleic acid binding pair may be digested with trypsin to produce a trypsin digest, where the resultant fragments are analyzed by tandem MALDI-TOF/ESI mass spectrometry to produce a searchable profile. Identification of the protein is then done by comparing the resultant profile to a database of reference profiles generated by a theoretical trypsin digest created against all available protein sequences in a given protein sequence database (for example, SWISS-PROT). Such a protocol is described in: Gygi, S. P et al. *Nat. Biotech.* (1999), Vol 17: 994–999, and Griffin, T. J. et al. Anal. Chem. (2001), Vol 73: 978–986. Other protein characterization protocols that may be employed include, but are not limited to: yeast two-hybrid protocols, protein fragment complementation assay protocols; and the like.

Where desirable, larger amounts of the protein member of the protein/nucleic acid binding pair may be obtained prior to characterization. Any convenient protocol for obtaining larger amounts of the to be characterized protein member may be employed. For example, one may be use the nucleic acid member of the pair to purify additional protein from the original source employed in the methods, as described above. For example, the nucleic acid member of the identified protein/nucleic acid binding pair may be amplified to produce solid phase capturable nucleic acids, e.g., the nucleic acid may be amplified using 5' end biotinylated gene specific primers. These resultant capturable nucleic acids can be employed to capture the protein member of interest, e.g., by contacting the capturable nucleic acids with a source of the protein to be identified, e.g., the cellular/tissue extract or lysate, under protein/nucleic acid binding conditions. The resultant complexes are then purified, e.g., by Streptavidin coated beads, to obtain purified amounts of the protein member for subsequent characterization. The above protein purification protocol is merely representative, as any convenient protocol may be employed. Other protocols of interest include, but are not limited to: Gygi, S. P et al. *Nat. Biotech.* (1999), Vol 17: 994–999; and the like.

Nucleic Acid Binding Sequence Identification

Figure 4:
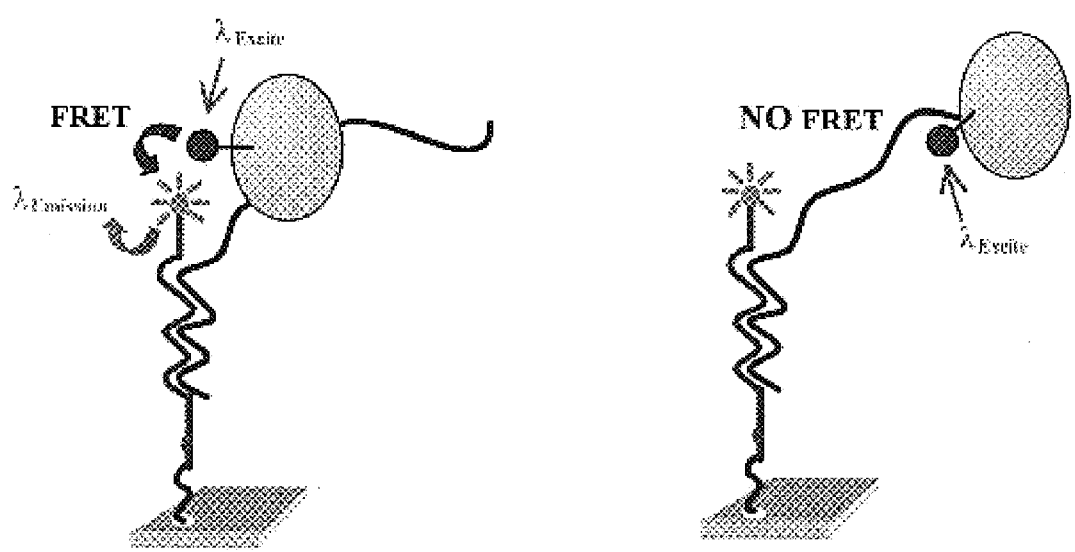
FIG. 4 provides an illustration of the effect of distance on the FRET relationship that can be established by the subject methods.

In certain embodiments, the binding sequence of the nucleic acid member may be characterized. In certain embodiments, as described above, the array employed in the subject methods includes a plurality of molecular beacon probes that each hybridize to the same target nucleic acid, where the distinct probe members of the plurality differ from each other by hybridizing to different locations of the target nucleic acid to which they hybridize. In those embodiments where a plurality of such probes are present for each target nucleic acid, e.g., it includes a tiled set of probes for a given target nucleic acid, some members of the probe set will give rise to a FRET signal and some will not, as illustrated in FIG. 4. By knowing the sequence of the target nucleic acid, as well as the sequence of the probe regions of the molecular beacon probes that do and do not give rise to a FRET signal, one can readily approximate the sequence of the protein binding domain of the target nucleic acid which is bound by the protein member of the protein/nucleic acid binding pair.

Utility

The subject methods of identifying protein/nucleic acid binding pairs can be used in a variety of different applications. Representative applications of interest include research applications, where the subject invention is employed to identify and characterize protein/nucleic acid binding pairs. As such, one can employ the subject invention to rapidly identify and characterize RNA/protein binding pairs, single-stranded DNA/protein binding pairs (where the protein members may be involved in DNA replication, repair, recombination, etc.), double-stranded DNA/protein binding pairs (where the protein members may be histones, transcription factors, methylases, polymerases, etc.), telomeric DNA/protein binding pairs, secondary structure (e.g., Z-DNA, G-quartet DNA, triplex DNA, cruciforms, etc.) assuming nucleic acid/protein binding pairs, etc., in various research applications, such as elucidation of biochemical pathways, e.g., cellular processes such as replication, transcription, signaling, etc.

Systems

Also provided are systems for use in practicing the subject methods. The systems typically include at least the following components which are employed in-practicing the subject methods: (a) a molecular beacon array; (b) protein labeling reagents, where the label of the labeling reagent and the label of the molecular beacon probes of the array make up FRET pair; (c) targets nucleic acid generation reagents; (d) a fluorescent signal detector. Specifics regarding each of these elements are provided above.

Kits

Also provided are kits for use in the subject invention. The kits typically include a molecular beacon array and at least one protein labeling reagent where the labeling reagent includes a fluorescent label that is selected to make up a FRET pair with the fluorescent label on the probes of the molecular beacon array, where FRET pairs are described above. In certain embodiments, the kits also include reagents necessary for generating the target nucleic acids, e.g., buffers, primers, polymerases, RNA isolation reagents, detergents, etc.

The various components of the kits may be present in one or more containers, each with one or more of the various reagents (sometimes in concentrated form) utilized in the methods.

Finally, the kits may further include instructions for using the kit components in the subject methods. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

The following examples are offered by way of illustration and not by way of limitation.

EXPERIMENTAL

I. Preparation of Molecular Beacon Arrays-Molecular Beacon Arrays are Prepared by the Following Methods.

A. Deposition

In one method, the individual oligonucleotide sequences labeled with the appropriate molecular beacons (fluorophore donors and acceptors) are prepared by conventional DNA synthesis on solid support using known methods, such as, but not limited to, the phosphoramidite strategy on CPG. When an additional synthetic moiety is necessary to anchor the sequences to a solid support, it is attached to the oligonucleotide sequence during the chemical synthesis of the individual probe, either at the 5' or 3' end, or in the center of the sequence. Those individually prepared probes are then deposited on solid supports, such as glass, by pulse-jet printing or by mechanical methods involving the contact between the solid support and a physical carrier (fiber optics, pins, etc.) to produce a molecular beacon array. Typically, the glass surface is functionalized prior to deposition with a mono or multilayer of a coating reactive with a natural or synthetic moiety within the oligonucleotide being deposited. The glass surface is optionally treated after deposition to covalently fix the DNA molecules and/or to inactivate the coating reactive groups that were not used in the attachment of the DNA sequences.B. In Situ Synthesis In another method, the molecular beacon probes are synthesized directly on the solid support, such as glass, in a spatially controlled manner to achieve the formation of individual features to produce a molecular beacon array. The synthesis is typically performed using the phosphoramidite synthetic methodology and the spatial control is achieved during the coupling step using pulse-jet printing technologies to deposit the phosphoramidite reagents. Other steps of the DNA synthesis cycle are performed in a flowcell without spatial control. Alternative methods may include the spatial control of the deblock step utilizing, for instance, light activation strategies using photolabile protection groups or photogenerated acids and bases. The solid support is typically functionalized with moieties reactive with the first DNA monomer coupled to the surface, such as hydroxyls or amino groups. At the end of the DNA synthesis, protecting groups, such as of the bases and phosphate groups, are removed under alkaline conditions which do not cleave the DNA probes from the surface.

The molecular beacon probes sequences are typically anchored to the surface by their 3' end, although existing chemistry permits the attachment at any location along the sequence, including the 5' end. A spacer is typically used between the molecular beacon DNA sequence and the attachment point of the probe with the solid support. Typical spacers include polyethylene glycol phosphates and polynucleotides of natural, such as T, and synthetic, such as such a basic, nucleic acid monomers. The fluorophore acceptor is typically placed between the spacer and the DNA sequence, and the fluorophore donor is typically placed at the other extremity of the DNA sequence. The DNA sequence of the first 8 bases and of the last 8 bases are chosen to be complementary to each other to form, in the absence of DNA target, the thermodynamically favored stem loop. The DNA sequence between the flanking stem sequences can be any sequence of natural and modified nucleic acids monomer necessary to capture the nuclei acid targets.

II. Preparation of Nucleic Acid Targets

Target nucleic acids are prepared using already established protocols (e.g., single stranded and double stranded c-DNA prepared by reverse transcription of mRNA.) Total RNA is prepared by precipitation of nucleic acids from cellular extracts and subsequent DNAseI digestion. cRNA is prepared by the method of U.S. Pat. No. 6,132,997, the disclosure of which is herein incorporated by reference.

III. Hybridization of Probe:Target Pair

Mix 2–5 μg of unlabeled target nucleic acid (see section II above) in a total volume of 300 μl of hybridization buffer (e.g., from Agilent, Palo Alto, Calif.) in a hybridization chamber. Incubate the chamber in a 60° C. rotisserie oven with mixing for a period of 12–17 hrs. Dismantle the array from the chamber at room temperature in a low stringency buffer such as 6×SSPE (containing 0.005% sodium lauryl sarcosine) and wash the array in the same buffer composition for 1 minute. Transfer the array to a fresh solution of high stringency buffer such as 0.06×SSPE and wash further for 30 seconds to dissociate non-specifically bound target molecules.

IV. Preparation of Labeled Proteins

This protocol will apply for a library of expressed His tagged proteins. Clone a specific cDNA library (from tissue samples being compared) in an appropriate expression vector cassette containing an in-frame histidine tag. Transfect cells (mammalian, bacterial, insect etc. . . . ) with this library allowing for expression of the individual His-Tagged proteins. Concentrate cells by centrifugation and resuspend in 1 ml of Lysis buffer (50 mM $NaH_2PO_4$, 300 mM NaCl, 10 mM imidazole, pH 8.0). Add lysozyme to a final concentration of 1 mg/ml. Incubate on ice for 30 minutes and sonicate mixture to lyse cells. Centrifuge lysate at 10,000×g for 30 minutes at 4° C. and collect the supernatant. Equilibrate Ni-NTA spin column with 600 μl of lysis buffer by centrifuging for~2 minutes at 700×g. Load an equivalent volume of lysate containing the His-tagged proteins onto this pre-equilibrated column and centrifuge for 2 minutes at 700×g. Wash the column twice with 600 μl of wash buffer (50 mM $NaH_2PO_4$, 300 mM NaCl, 20 mM imidazole, pH 8.0) and centrifuge for 2 minutes at 700×g. Elute the His-tagged proteins twice with 200 μl of elution buffer (50 mM $NaH_2PO_4$, 300 mM NaCl, 250 mM imidazole, pH 8.0) and collect the eluate.

Label the proteins using the appropriate "protein labeling kit" available from Molecular Probes, Inc. and its associated protocol (e.g., FLUOROSCEIN-EX™ Protein Labeling Kit").

V. Binding Labeled Proteins to Hybridized Array

Perform labeled protein binding experiments by titrating, for each molecular beacon array, a specific concentration of purified labeled proteins (2–10 μg) under physiological buffer conditions (50 mM $NaH_2PO_4$, 100 mM NaCl, 1 mM $MgCl_2$, 1 mM $ZnCl_2$, 1 mM $CaCl_2$, and protease inhibitors, pH 7.0–8.0) for a period of 1 hour at 37° C. Gently wash the protein bound array with the binding buffer (50 mM $NaH_2PO_4$, 100 mM NaCl, 1 mM $MgCl_2$, 1 mM $ZnCl_2$, 1 mM $CaCl_2$, and protease inhibitors, pH 7.0–8.0) for 30 sec.

It is evident from the above results and discussion that the subject invention provides a number of advantages over the current nucleic acid/protein binding pair characterization protocols described in the Background of the Invention Section, above. Unlike LMPCR/TDPCR where sequence information is required to footprint the protein-nucleic acid contacts, the subject microarray based technology outlined in this invention has this information built-in (as the sequence of the transcript/probe attached on the surface). In addition, unlike LMPCR/TDPCR, this technology is technically less challenging and can easily be practiced by those with moderate familiarity with microarrays, gene expression profiling and protein expression, purification, and labeling. Furthermore, one of the major advantages of this invention is that, unlike LMPCR/TDPCR, this technology is very high throughput and can identify numerous different protein(s) that bind to different features (each feature representing a particular transcript). LMPCR and TDPCR are not at all amenable to high throughput analysis and require several days for data processing. As such, the subject invention represents a significant contribution to the art.

All publications and patent application cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of identifying protein/nucleic acid binding pairs, said method comprising:

(a) contacting a molecular beacon array comprising a plurality of distinct molecular beacon probes with a population of target nucleic acids to produce a hybridized molecular beacon array, wherein each distinct probe of said plurality comprises a different probe sequence and all of said probes of said plurality share a common first fluorescent label;

(b) contacting said hybridized molecular beacon array with a population of fluorescently labeled proteins to produce a protein bound array, where each member of said population of fluorescently labeled proteins is labeled with a second fluorescent label that makes up a FRET pair with said first fluorescent label; and (c) detecting any FRET generated signals from said array to identify protein/nucleic acid binding pairs on said array.

2. The method according to claim 1, wherein said method further comprises detecting any fluorescent signal from said hybridized array prior to step (b) to identify target nucleic acids hybridized to said hybridized array.

3. The method according to claim 1, wherein said method further comprises characterizing the protein of a protein/nucleic acid binding pair identified by said method.

4. The method according to claim 1, wherein said method further comprises characterizing the protein binding sequence of a nucleic acid of a protein/nucleic acid binding pair identified by said method.

5. The method according to claim 1, wherein said target nucleic acid and fluorescently labeled protein populations are generated from the same tissue/cellular source.

6. The method according to claim 1, wherein said target nucleic acid and fluorescently labeled protein populations are generated from different tissue/cellular sources.

7. The method according to claim 1, wherein said hybridized array is contacted with two differentially labeled protein populations.

8. The method according to claim 7, wherein said two differentially labeled protein populations make up a test/control pair.

9. The method according to claim 8, wherein said two differentially labeled protein populations make up a normal/disease pair.

10. The method according to claim 1, wherein said molecular beacon array comprises two or more distinct molecular beacon probes that hybridize to the same target nucleic acid, wherein said two or more distinct probes differ from each other by hybridizing to different locations of said target nucleic acid.

11. the method according to claim 1, wherein said method minter comprises a data transmission step in which a result from a reading of the array is transmitted from a first location to a second location.

12. The method according to claim 11, wherein said second location is a remote location.

13. A method comprising receiving data representing a result of a reading obtained by the method of claim 1.

14. A system for use in identifying protein/nucleic acid binding pairs, said system comprising:
   (a) a molecular beacon array comprising a plurality of distinct molecular beacon probes, wherein each distinct probe of said plurality comprises a different probe sequence and all of said probes of said plurality share a common first fluorescent label;
   (b) a labeling reagent for labeling a protein population with a second fluorescent label, wherein said first and second labels make up a FRET pair;
   (c) reagents for generating a population of target nucleic adds, and
   (d) a fluorescence detector device.

15. The system according to claim 14, wherein said molecular beacon array comprises two or more distinct molecular beacon probes that hybridize to the same target nucleic acid, wherein said two or more distinct probes differ from each other by hybridizing to different locations of said target nucleic acid.

16. The system according to claim 14, wherein said system includes two different labeling reagents for producing two differentially labeled protein populations that are each labeled with a different second fluorescent label that makes up a FRET pair with said first fluorescent label.

17. The system according to claim 14, wherein said fluorescence detector device is a fluorescent scanner.

18. The system according to claim 14, wherein said system further comprises reagents necessary for identifying a protein component of an identified protein/nucleic acid binding pair.

19. A kit for use in identifying protein/nucleic acid binding pairs, said kit comprising:
   (a) a molecular beacon array comprising a plurality of distinct molecular beacon probes, wherein each distinct probe of said plurality comprises a different probe sequence and all of said probes of said plurality share a common first fluorescent label;
   (b) a labeling reagent for labeling a protein population with a second fluorescent label, wherein said first and second labels make up a FRET pair; and
   (c) reagents for generating a population of target nucleic acids.

20. The kit according to claim 19, wherein said molecular beacon array comprises two or more distinct molecular beacon probes that hybridize to the same target nucleic acid, wherein said two or more distinct probes differ from each other by hybridizing to different locations of said target nucleic acid.

21. The kit according to claim 19, wherein said kit includes two different labeling reagents for producing two differentially labeled protein populations that are each labeled with a different second fluorescent label that makes up a FRET pair with said first fluorescent label.

22. The kit according to claim 19, wherein said kit further comprises reagents necessary for identifying a protein comprising of an identified protein/nucleic acid binding pair.

23. A substrate comprising a surface having at least one protein/nucleic acid binding pair immobilized thereon, wherein each protein/nucleic acid binding pair comprises:
   (a) a molecular beacon probe comprising a first fluorescent label;
   (b) an unlabeled target nucleic acid hybridized to said molecular beacon probe; and
   (c) a fluorescently labeled protein labeled with a second fluorescent label and bound to said unlabeled target nucleic acid, wherein said second fluorescent label and said first fluorescent label make up a FRET pair.

24. The substrate according to claim 23, wherein said substrate comprises two or more different protein/nucleic acid binding pairs immobilized on said surface.

25. A method of identifying protein/nucleic acid binding pairs, said method comprising:
   (a) contacting a nucleic acid probe array comprising a plurality of distinct probe nucleic acids with a population of target nucleic acids to produce a hybridized array, wherein each distinct probe nucleic acid of said plurality comprises a different probe sequence;
   (b) contacting said hybridized array with a population of labeled proteins to produce a protein bound array; and
   (c) detecting any surface bound protein/target nucleic acid complexes to identify protein/nucleic acid binding pairs on said array.

26. The method according to claim 25, wherein said labeled proteins are labeled with a first fluorescent label.

27. The method according to claim 26, wherein said target nucleic acids are labeled with a second fluorescent label, wherein said first and second fluorescent labels make up a FRET pair.

28. The method according to claim 25, wherein said labeled proteins arc labeled with an indirectly detectable label.

29. The method according to claim 25, wherein said method further comprises contacting said hybridized array with a second population or labeled proteins that arc distinguishably labeled from said first population of labeled proteins.

30. A method of identifying protein/nucleic acid binding pairs, said method comprising:
   (a) contacting a molecular beacon array comprising a plurality of distinct molecular beacon probes with a population of target nucleic acids to produce a hybridized molecular beacon array, wherein each distinct probe of said plurality comprises a different probe sequence and all of said probes of said plurality share a common first fluorescent label;

(b) contacting said hybridized molecular beacon array with at least one fluorescently labeled protein to produce a protein bound array, where said at least one fluorescently labeled protein is labeled with a second fluorescent label that makes up a FRET pair with said first fluorescent label; and (c) detecting any FRET generated signals from said array to identify protein/nucleic acid binding pairs on said array.

31. A method of identifying protein/nucleic acid binding pairs, said method comprising:

(a) contacting a nucleic acid probe array comprising a plurality of distinct probe nucleic acids with a population of target nucleic acids ro produce a hybridized array, wherein each distinct probe nucleic acid of said plurality comprises a different probe sequence;

(b) contacting said hybridized array with at least one labeled protein to produce a protein bound array; and (c) detecting any surface bound protein/target nucleic acid complexes to identify protein/nucleic acid binding pairs on said array.

* * * * *